United States Patent [19]

Weaver

[11] 4,401,755
[45] * Aug. 30, 1983

[54] PROCESS FOR MEASURING MICROBIOLOGICALLY ACTIVE MATERIAL

[75] Inventor: James C. Weaver, Sudbury, Mass.

[73] Assignee: Massachusetts Institute of Technology, Cambridge, Mass.

[*] Notice: The portion of the term of this patent subsequent to Aug. 16, 2000 has been disclaimed.

[21] Appl. No.: 229,483

[22] Filed: Jan. 29, 1981

[51] Int. Cl.$^3$ .................... C12Q 1/04; C12Q 1/18; C12Q 1/06; C12M 1/34

[52] U.S. Cl. .................... 435/34; 435/32; 435/39; 435/291; 435/808; 435/29

[58] Field of Search .................... 435/34, 39, 291, 808, 435/32, 29

[56] References Cited

U.S. PATENT DOCUMENTS

| | | | |
|---|---|---|---|
| 3,560,754 | 2/1971 | Kamentsky | 55/101 X |
| 3,710,933 | 1/1973 | Fulwyler et al. | 424/3 X |
| 3,790,492 | 2/1974 | Fulwyler | 264/0.5 X |
| 4,162,282 | 7/1979 | Fulwyler et al. | 264/10 X |
| 4,242,447 | 12/1980 | Findl et al. | 435/291 X |

*Primary Examiner*—Robert J. Warden
*Attorney, Agent, or Firm*—Arthur A. Smith, Jr.; Paul J. Cook; Thomas J. Engellenner

[57] ABSTRACT

The activity of a microbiologically active material is measured by suspending the material in a liquid medium capable of forming a gel. The resultant suspension is formed into small liquid droplets which droplets are caused to gel. The gel microdroplets (GMDs) are treated to effect desirable alteration of the microbiologically active material and the amount of metabolites or reaction products of the desired alteration within each get droplet is measured. Alternatively, incubation is carried out such that each GMD initially containing one cell contains many, a microcolony, which can be tested for desirable properties while retaining sufficient viable cells for with growth and harvesting for further testing and/or production.

25 Claims, No Drawings

PROCESS FOR MEASURING MICROBIOLOGICALLY ACTIVE MATERIAL

BACKGROUND OF THE INVENTION

This invention relates to a process of performing measurements on microbiologically active material such as bacteria.

Presently, in the field of rapid detection or measurement of microbial activity, there is available a wide variety of apparatus and processes. Generally, these are based on the measurement of the physical characteristics of many viable cells (microorganisms), the growth of individual cells into many viable cells, or the growth and metabolism of many viable cells, or the composition of many cells. Examples of measurements of the physical characteristics of many cells include light attenuation (turbidity), light scattering and viscosity. Examples of the measurement of the growth of individual cells into many cells includes culturation on a petri dish or other gel surface or culturation in a gel contained in an optically transparent capillary. Examples of the measurement of the growth and metabolism of many viable cells includes measurement of pH changes of the medium containing the viable cells, measurement of non-radioactive accumulated volatile metabolites in the headspace over a sample, measurement of heat production, or measurement of electrical conductivity of the medium containing the viable cells. An example of staining includes the measurement of fluorescent labeled antibody, the antibody binding to species specific surface antigens on the cells. An example of the measurement of the composition of many cells is pyrolysis/mass spectroscopy, which method is destructive in that it rapidly fragments cells under conditions of high temperature.

While the present procedures are highly satisfactory in many respects, two important problems exist. First, procedures which measure the growth of individual cells into many cells, such as culturation in a gel, have the highly desirable feature that they do provide an enumeration or count of the original number of viable cells present in a sample, but have the undesirable feature that they require a long incubation time, often 12 to 48 hours, to obtain a measurable colony from an original cell. This long incubation is also required for the measurement of the physical characteristics of many cells for the composition of many cells since it is generally not possible to obtain a sufficiently pure sample, free of debris and other cell types, without culturation. Further, measurement of the metabolism of many cells also requires a lengthy incubation time if the cell density in the sample is initially small. Second, procedures which measure the physical characteristics of many cells, the composition of many cells or the growth and metabolism of many cells do not provide an enumeration or count of the cells present, since there is often considerable variability between the individual cells. An important example is a variable and unknown lag time which often occurs when measurement of growth and metabolism of many cells is employed with a sample containing a small initial number of cells. In this case, a variable lag time can lead to the inability to correlate the subsequently measured growth and metabolism of many cells with the enumeration or count of the initial cells. A particularly undesirable occurance is the presence of initially stressed or injured cells which have a long, but a priori unknown, lag time, since the result of the measurement in this case is a false negative.

It has been proposed by Rotman, *Proceedings National Academy of Sciences,* Vol. 47, Pages 1981–1991, 1961 who discloses the formation of water droplets in oil which droplets contain a small number of enzymes. However, this procedure is very tedious, difficult to replicate and the enzymes are susceptible to migration from the droplets to the oil-water interface.

SUMMARY OF THE INVENTION

In accordance with this invention, a sample containing an unknown quantity of microbiologically active materials having a size ranging from molecular size to about three microns are suspended at a slightly to highly dilute concentration in a medium which can be subsequently converted to a gel medium. The suspending medium is capable of substantially preventing degradation of the microbiologically active molecules or of supporting growth of the microbiologically active matter such as bacteria. The dilute suspension is formed into small droplets such as by being forced through a nozzle to form a liquid stream which then is sheared to form small liquid droplets, each of which has a high probability of containing a desired small number, or less, of molecules or cells. Thus, for example, each droplet can contain zero or one microbiologically active molecule or cell of interest with or without microbiologically active molecules which coact with the molecule of interest by regulating the degree of dilution of the liquid composition processed and the average size of GMDs produced. The droplets formed then are changed in temperature or are directed into a second liquid or vapor medium wherein the droplets rapidly gel. The change in temperature or second vapor or liquid medium is capable of converting the droplets to gel form while preventing degradation of the microbiologically active material. Alternatively, the liquid droplets are caused to gel before encountering the second vapor or liquid medium. In this case, the gel micro-droplets (GMDs) can be directed onto a solid surface. The GMDs are treated in a manner to effect a desirable alteration of the microbiologically active material such as by incubation or by exposure to conventional marker molecules such as a fluorescent stain or by exposure to a mutagenic environment the like. Either before or after such treatment, the GMDs can be coated with a thin layer of material such that the thin layer is impermeable to small molecular weight metabolites or products of specific enzymes or the like. Following an incubation interval during which time metabolites or specific reaction products are accumulated and retained within the GMDs, and during which time a corresponding change of physical or chemical characteristics occurs, such as a fluorescence shift due to a pH change, or due to metabolite accumulation or accumulation of a fluorescent product of a specific enzyme reaction, the GMDs are passed through a suitable measuring device capable of monitoring the changed physical characteristic, such as in a suspension through a flow microfluorometer. The suspension of GMDs suitably diluted is processed through an apparatus which forms a stream of the micro-droplets and the GMDs pass an analyzer one by one so that each GMD can be analyzed for a desired chemical or physical characteristic. Furthermore, if desired, the apparatus is capable of separating gel micro-droplets having the desired characteristics from the remainder of the stream in response to a signal from the onstream analyzer. Alternatively, measurements can be made on GMDs on a surface by scanning with a suitable light source or other means, in order to measure for desirable phyiscal characteristics.

DESCRIPTION OF SPECIFIC EMBODIMENTS

In accordance with this invention, microbiologically active materials having a small size such as yeast, bacteria, mold, enzymes or the like are suspended in an aqueous medium capable of gelatin upon subsequent treatment of the suspending medium.

Suitable suspending mediums include water soluble natural gel material and synthetic water soluble polymers. Representative suitable materials include kappa-carrageenan, iota-carrageenan, sodium alginate, furcellaran, zein, succinylated zein, succinylated cellulose or the like. Representative suitable synthetic water soluble polymers include those formed from vinyl pyrolidone, ethyl succinate cellulose 2-methyl-5-vinyl pyrridine-methyl acrylate-methacrylate acid copolymer, vinyl alcohol, vinyl pyrridine, vinyl pyrridine-styrene copolymer or the like. The microbiologically active material is suspended in the suspending medium at a dilution which is selected using knowledge of the volume of the GMD to be produced and an estimate of the density or size of cells or molecules in the first liquid medium.

The GMDs are formed so that there is a high probability that each GMD contains a desired number or less of microbiologically active material. This can be effected by regulating the dilution of the liquid composition to be produced to GMDs, a knowledge of the size of the microbiologically active material and the size of the GMDs to be produced. The regulation of these factors can be determined by conventional Poisson statistical analyses so that the number of GMDs containing more that the desired number of microbiologically active materials is more than two standard deviations from the mean. It is desirable, for example, to isolate zero to one microbiologically active cell per GMD in recombination DNA research where it is desired to isolate a particularly active genetically enzyme bacterium from a large population of such bacterium.

Gel material and nutrients can be incorporated in the suspending medium, in which case very little dilution may be desired. Thus, for example, when it is desired to have a high probability of zero to one microbiologically active material per GMD, it is only necessary to dilute the sample by more than about a factor of about 1.1, usually up to about 10 or larger if desired if the unknown cell or enzyme concentration is believed to be large. For example, if the average volume ($V_{GMD}$) is about $10^{-7}$ ml, corresponding to a GMD with diameter about $5 \times 10^{-3}$ cm (50 $\mu$m), is spherical, dilution is generally not needed until the initial cell concentration reaches about $10^{-7}$ calls-ml$^{-1}$, which is a much higher concentration than encountered for most samples. For smaller spherical GMDs, for example, 10$\mu$ diameter, dilution is not needed until the sample concentration reaches about $10^9$ cells-ml$^{-1}$.

For purposes of measuring microbiologically active material, it is desirable to utilize dilutions such that the suspension can be subsequently formed into droplets each of which have a high probability of containing none of the desired microbiologically active material of interest or only a single cell or molecule of the microbiologically active material of interest. By separating and localizing the microbiologically active material in this manner, it is possible to measure materials of desired activity which activity is not diluted by the presence of other biologically active material not having the desired activity. For example, it may be desirable to measure bacteria such as *E. coli* in accordance with the process of this invention in unknown quantity. The bacteria is suspended in a medium capable of forming a gel upon subsequent treatment and then converted into droplets such that there is a high probability that each droplet contains none or only one of such bacteria. The thus-produced liquid droplets are directed into a liquid medium capable of effecting gelation of the droplets. Alternatively, the initially liquid droplets are changed in temperature or contacted with suitable gel-inducing vapors before entering a second liquid medium. In addition, the gel droplets also can contain a conventional bacteria growth supporting composition which permits the bacteria to metabolize and, sometimes, to replicate within the droplets, and can also contain indicator compounds such as dyes whose fluorescence changes with pH.

In the case of uncoated GMDs, the suspension of such gel droplets then is treated in a conventional manner such as with a fluorescent dye, a fluorescent labeled antibody or fluorescent labeled antigen or the like in order to mark the gel droplets having bacteria whose measurement is desired while preventing or greatly reducing marking of the gel droplets not containing the desired bacteria. In the case of coated GMDs, the first suspending medium is provided with specific nutrients or specific substrates or the like, in addition to any indicator dyes or pH shifts, in order to allow measurement of specific cells or enzymes.

This invention is useful for studying a wide variety of materials having microbiological activity, interaction or suppression including parasites, virus, yeast, cells, bacteria mold, enzymes, interactions between variant cells, cell-virus interactions, hybridomas or the like.

Representative bacteria which can be processed in accordance with this invention include *E. coli*, Bacillis Subtilis, Pseudomonas species, *Clostridium thermocellum, Zymomanas mobilis, Methano bacterium sochngenic, Salmonella typhimurium, Serratic macens, Clostridium botulinum, Bacillis sterothermophidis.* Conventional tagging means can be utilized in order to identify uncoated gel droplets containing the bacteria having the desired characteristics including radioactively labeled antibody, fluorescent antibody labeling, use of fluorescent dyes, viable stains, magnetic labeling of the droplets. These procedures are well known to be selective in labeling and/or staining surface properties or internal pathways of bacteria. Similarly, the same techniques can be utilized for selectively identifying yeast, mold, parasites, etc.

In the case of molecular size biologically active molecules such as enzymes, NADA or other fluorescent products or cofactors can be measured; the following procedure can be utilized in accordance with this invention. A sample containing an unknown quantity of a particular enzyme is suspended, with modest or large dilution, in a first liquid medium which contains buffering compounds (if desired), substrates, cofactors and a gelling agent. When the approximate upper limit of the concentration of enzymes to be measured can be estimated, a GMD volumes is selected so that there is a high probability the GMDs will contain either none or one enzyme molecule. If a linked enzyme assay is used, the appropriate assay is used; the appropriate additional enzymes. substrates and cofactors are also included at a relatively high concentration. Similarly, if an assay is to be based on cell-cell interactions, one type of cell is also provided at relatively high concentration. The resulting diluted sample is then passed through a vibrating orifice or nozzle to cause formation of liquid droplets. As described previously, the liquid droplets are caused to enter the gel state by cooling, contacting with a suitable vapor, or entering a second liquid medium. The resulting GMDs are coated with a thin layer impermeable or having controlled permeability, to the substrates, products and cofactors of the enzyme catalyzed reaction, such as phosphatidyl ethanolamine or phosphatidyl choline or the like. For example, the permeability of the coating can be controlled to allow entry into the GMDs of a reagent that effects marking, lysing or the like within the GMD and restricts outflow from the GMD of such marked product. The coated GMDs are maintained at a suitable temperature such that the enzyme reactions are carried out, not necessarily to completion, and fluorescent product is accumulated and retained in GMDs containing an enzyme molecule. Alternatively, a fluorescent substrate can be utilized, in which case the fluorescent substrate decreases or disappears in GMDs containing an enzyme molecule.

After the biologically active material within the gel micro-droplets has been treated in order to effect the desired change in the material, such as by incubation, mutation, staining with fluorescent stains, labeled with magnetically tagged or other immunological agents, the suspension of the gel micro-droplets then is processed in an apparatus having the capability of sensing a physical characteristic of individual gel micro-droplets to determine the presence or absence of a desired physical characteristic and thereafter isolating the gel micro-droplets having the desired physical characteristic. For example, the desired gel micro-droplets may be selectively stained with a fluorescent dye and can be passed one by one in a liquid stream by an optical analyzer capable of sensing the concentrated fluorescent dye on the gel micro-droplet. The analyzer controls means for isolating that portion of the liquid stream which satisfies the sensing criteria. For example, a portion of the liquid stream can be diverted into a secondary stream for subsequent recovery of the gel micro-droplets such as is disclosed by Kamentsky, U.S. Pat. No. 3,560,754. Alternatively, the mainstream can be converted into discrete droplets by being passed through a nozzle which is vibrated such as by a piezoelectric crystal by the means disclosed for example by Fulwyler, U.S. Pat. Nos. 3,710,933, 3,790,492 and 4,162,282. The drops containing the gel micro-droplets having the desired characteristics then can be electrically charged selectively and then passed between a pair of deflecting plates in order to selectively divert the electrically charged droplets so that they can be recovered.

The process of this invention provides substantial advantages over the prior art processes in that microbiologically active material having a size much smaller than that of the normal cell, usually within the range of about 5 to 0.5 microns and even as small as molecular size materials, can be measured and used, if desired, to isolate or recover microbiologically active materials having a desired characteristic from a large population of such microbiologically active materials, the majority of which do not have the desired microbiological characteristic.

EXAMPLE I

In this example a sample containing a small but unknown number of $E.$ $coli$ bacteria is diluted slightly, by a factor of about 1.1 to 10, by mixing the sample with solution containing nutrient medium, a pH indicator dye such as fluorescein or acridine, and sodium alginate such that the final mixture of sample plus diluent has nutrient concentrations 0.07 g/l, $Na_2HPO_4$, 0.03 g/l $KHPO_4$, 0.5 g Nad, 0.1 g$NH_1$d, 0.25 g Mg $SO_4.7H_2O$, 0.2% glucose, supplemented with 0.04 Molar Nad, 1% glucose, 1% vitamins free casamino acid and Vitamin B1 and a sodium alginate concentration of about 2%. The suspension then is passed through a vibrating orifice or nozzle such that the liquid stream breaks up into liquid droplets. The liquid droplets are directed into a second liquid medium, typically stirred gently, of $5 \times 10^{-1}$ M $CaCl_2$ at pH 7, where said liquid droplets rapidly exchange Na ion with Ca ions and become GMDs. Gel formation typically occurs first at the outer surface of said liquid droplets, forming a temporary, deformable skin, which deformable skin allows interfacial forces to direct the droplet into an approximately spherical or ellipsoidal shape before the droplet is completely gelled. Within less than 1 to 15 minutes, depending on the $CaCl_2$ concentration, the transition into the gel state is complete. The GMDs are maintained in suspension by gently stirring, and then coated with a thin layer which is impermeable to small metabolites such as lactic acid. Suitable material is a lipid material such as phosphatidyl ethanolamine or phosphatidyl choline. A coated GMD which is occupied by a single cell accumulates the lactic acid metabolite and/or other metabolite such that the concentration of the metabolite increases rapidly because of the small volume of a coated GMD. A GMD with volume of about $10^{-7}$ ml, corresponding to a diameter of 35 $\mu$m, if spherical, increases matabolite concentration at about the same rate as a suspension of cells at a cell concentration of $10^{-7}$ cell-$ml^{-1}$. The metabolite accumulates at a rate that causes an initial, relatively unbuffered internal GMD pH of 7 to drop to 5.5 or lower in about 10 to 60 minutes or less after any lag time has elapsed. Typical metabolic lag times for $E.$ $coli$ are 10 to 60 minutes. Following a suitable incubation time of about 20 to 120 minutes or less, the suspension of coated GMDs is passed through a flow microfluorometer, such that coated GMDs with their internal pH at 5.5 or less are detected and counted by the altered fluorescence of the entrapped pH sensitive dye fluorescein or acridine. This measurement process produces a rapid enumeration or count based on non-destructive metabolic measurements on single cells. For confirmation or for testing of the presence of some cells with long lag times, the sample of coated GMDs are retained, incubated further, and passed through a flow microfluorometer a second time, such that both the original altered pH GMDs and more recent, due to the second incubation, altered pH GMDs are counted. Use of more than one incubation and passage through the flow microfluorometer provides a good, non-destructive test for the presence or absence of stressed or injured cells with lengthened lag times.

What is claimed:

1. The process of measuring the microbiological activity of a sample of a given material comprising the steps of:

(a) forming mutually independent samples of said material by
  (i) forming a dilute suspension of said material in a liquid diluent capable of forming a gel upon subsequent treatment, said dilute suspension having a dilution selected so that there is provided a high probability that each microsample produced from said suspension contains one or less microbiologically active molecule or cell,
  (ii) converting said suspension into gel droplets having a size between about 0.2 and 1000 microns, and
(b) measuring a product of microbiological activity of each of said gel droplets independently of the other of said droplets.

2. The process of claim 1 wherein said droplets have a size between about 5 and 100 microns.

3. The process of claim 2 wherein said bacterium is *E. coli*.

4. The process of claim 3 wherein said bacterium includes a genetically modified plasmid.

5. The process of claim 1 wherein said biologically active material is a bacterium.

6. The process of claim 1 wherein said biologically active material is an enzyme.

7. The process of claim 1 wherein said biologically active material is a yeast.

8. The process of claim 1 wherein said biologically active material is a mold.

9. The process of claim 1 wherein said material comprises an animal cell.

10. The process of claim 1 wherein said material comprises a plant cell.

11. The process of any one of claims 1, 2, 5, 3, 4, 6, 7, 8, 9 or 10 wherein the microbiologically active material having the desired characteristic is selectively tagged with a marker composition capable of being sensed and sensing said marker composition.

12. The process of any one of claims 1, 2, 5, 3, 4, 6, 7, 8, 9 or 10 wherein the microbiologically active material having the desired characteristic produces a metabolite capable of being sensed and sensing said metabolite.

13. The process of any one of claims 1, 2, 5, 3, 4, 6, 7, 8, 9 or 10 wherein the microbiologically active material having the desired characteristic coacts with a reagent within said micro-droplet to produce a reaction product capable of being sensed and sensing said reaction product.

14. The process for sensing the microbiological activity of a sub-sample having a desired microbiological characteristic from a large population of microbiologically active sub-samples lacking said desired characteristic which comprises forming a dilute suspension of said population in a liquid diluent capable of forming a gel upon subsequent treatment, said dilution being selected so that there is provided a high probability that each sub-sample produced from said suspension contains one or less microbiologically active molecule or cell, converting said suspension into gel droplets having a size between about 0.2 microns and about 1000 microns and sensing the gel droplets containing the microbiologically active material having the desired characteristic.

15. The process of claim 14 wherein said material is a bacterium.

16. The process of claim 15 wherein said bacterium is *E. coli*.

17. The process of claim 16 wherein said bacterium includes a genetically modified plasmid.

18. The process of claim 14 wherein said material is an enzyme.

19. The process of claim 14 wherein said material is a yeast.

20. The process of claim 14 wherein said material is a mold.

21. The process of claim 14 wherein the material comprises an animal cell.

22. The process of claim 14 wherein the material comprises a plant cell.

23. The process of any one of claims 14, 15, 16, 17, 18, 19, 20, 21 or 22 wherein the microbiologically active material having the desired characteristic is selectively tagged with a marker composition capable of being sensed and sensing said marker composition.

24. The process of any one of claims 14, 15, 16, 17, 18, 19, 20, 21 or 22 wherein the microbiologically active material having the desired characteristic produces a metabolite capable of being sensed and sensing said metabolite.

25. The process of any one of claims 14, 15, 16, 17, 18, 19, 20, 21, or 22 wherein the microbiologically active material having the desired characteristic coacts with a reagent within said micro-droplet to produce a reaction product capable of being sensed and sensing said reaction product.

* * * * *